(12) United States Patent
Kornerup

(10) Patent No.: US 6,679,882 B1
(45) Date of Patent: Jan. 20, 2004

(54) ELECTROSURGICAL DEVICE FOR COAGULATING AND FOR MAKING INCISIONS, A METHOD OF SEVERING BLOOD VESSELS AND A METHOD OF COAGULATING AND FOR MAKING INCISIONS IN OR SEVERING TISSUE

(75) Inventor: Niels Kornerup, Rungsted (DK)

(73) Assignee: Lina Medical APS, Glostrup (DK)

(*) Notice: Subject to any disclaimer, the term of this patent is extended or adjusted under 35 U.S.C. 154(b) by 0 days.

(21) Appl. No.: 09/715,666

(22) Filed: Nov. 17, 2000

Related U.S. Application Data

(63) Continuation-in-part of application No. 09/310,773, filed on May 10, 1999, now abandoned, which is a continuation-in-part of application No. PCT/DK98/00276, filed on Jun. 22, 1998.

(51) Int. Cl.[7] ............................................... A61B 18/18
(52) U.S. Cl. .......................................... 606/51; 606/46
(58) Field of Search ............................ 606/41, 42, 45, 606/46, 48–52, 205, 206

(56) References Cited

U.S. PATENT DOCUMENTS

| | | | |
|---|---|---|---|
| 2,031,682 A | | 2/1936 | Wappler et al. |
| 4,590,936 A | * | 5/1986 | Straub et al. ............... 606/111 |
| 5,190,541 A | * | 3/1993 | Abele et al. .................. 604/35 |
| 5,267,998 A | | 12/1993 | Hagen |
| 5,269,780 A | * | 12/1993 | Roos ........................... 606/42 |
| 5,403,312 A | | 4/1995 | Yates et al. |
| 5,423,809 A | * | 6/1995 | Klicek .......................... 606/38 |
| 5,443,463 A | * | 8/1995 | Stern et al. ................... 606/51 |
| 5,445,638 A | | 8/1995 | Rydell et al. |
| 5,456,684 A | * | 10/1995 | Schmidt et al. ............... 604/35 |
| 5,458,598 A | * | 10/1995 | Feinberg et al. ............. 606/205 |
| 5,527,331 A | * | 6/1996 | Kresch et al. ................ 604/22 |
| 5,674,220 A | | 10/1997 | Fox et al. |
| 5,716,366 A | | 2/1998 | Yates |
| 5,735,849 A | * | 4/1998 | Baden et al. ................ 606/205 |

FOREIGN PATENT DOCUMENTS

| | | |
|---|---|---|
| EP | 0 695 535 A1 | 2/1996 |
| WO | 97/18766 A1 | 5/1997 |

* cited by examiner

Primary Examiner—Michael Peffley
(74) Attorney, Agent, or Firm—Merchant & Gould P.C.

(57) ABSTRACT

An electrosurgical device for coagulating and for making incisions in or severing tissue such as blood vessels, the device comprising forceps jaws (6, 7) for immobilizing a tissue portion to be coagulated and incised, the forceps jaws (6, 7) being connected to means for applying an electrical tension between said forceps jaws for coagulating the tissue portion, the device further comprising a member (22) for being displaced between said forceps jaws (6, 7) to incise a tissue portion held between the forceps jaws and coagulated thereby, the member (22) being connected to means for applying an electrical voltage to said member for performing an incision in said tissue by means of said electrical voltage applied to said member (22) the member (22) preferably being blunt such that the incision substantially exclusively is achieved by means of the voltage applied to the member (22). For preventing the generation of smoke through charring of the tissue portion, a tube is provided for supplying an electrically non-conductive, cooling liquid to the tissue portion.

74 Claims, 5 Drawing Sheets

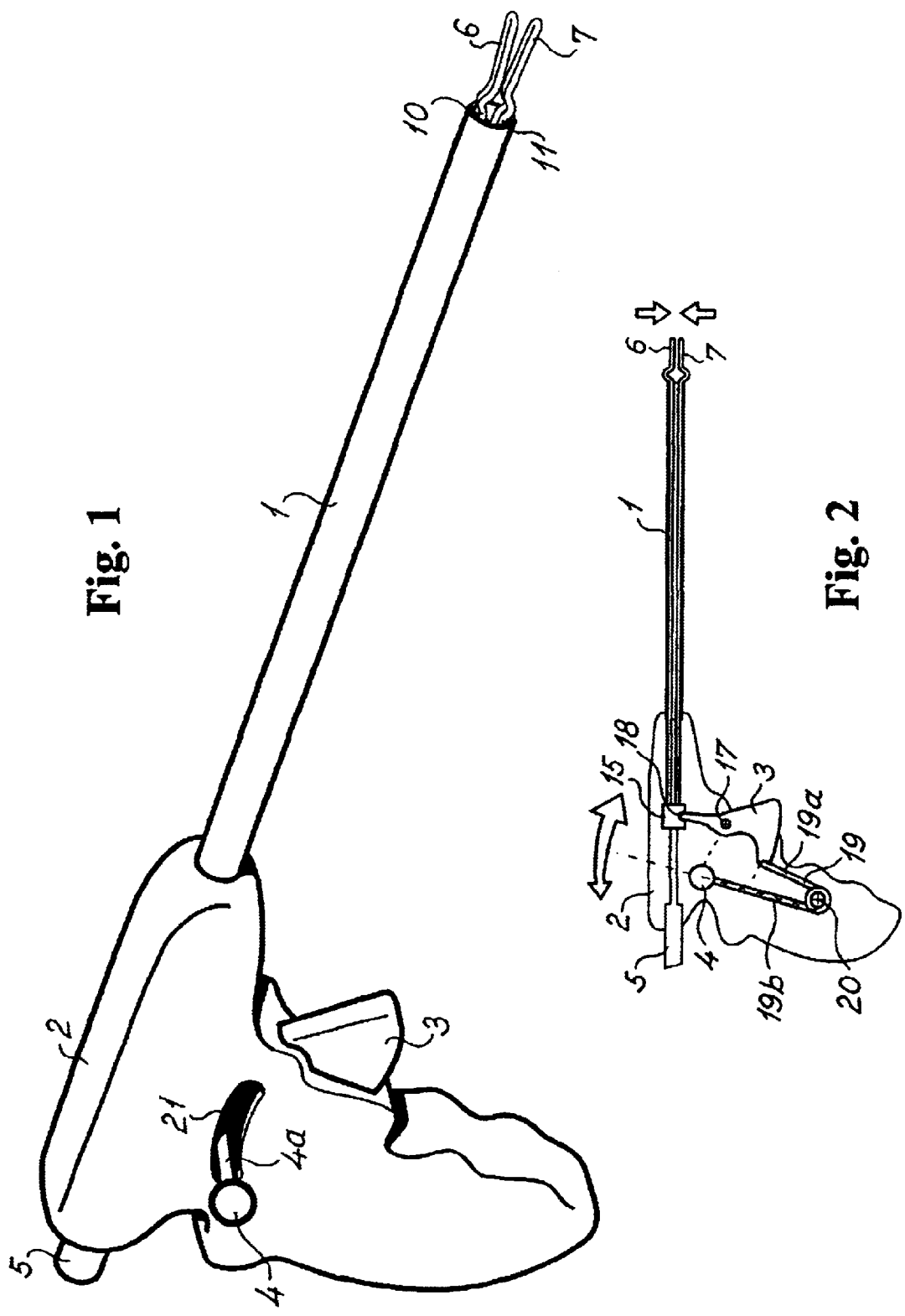

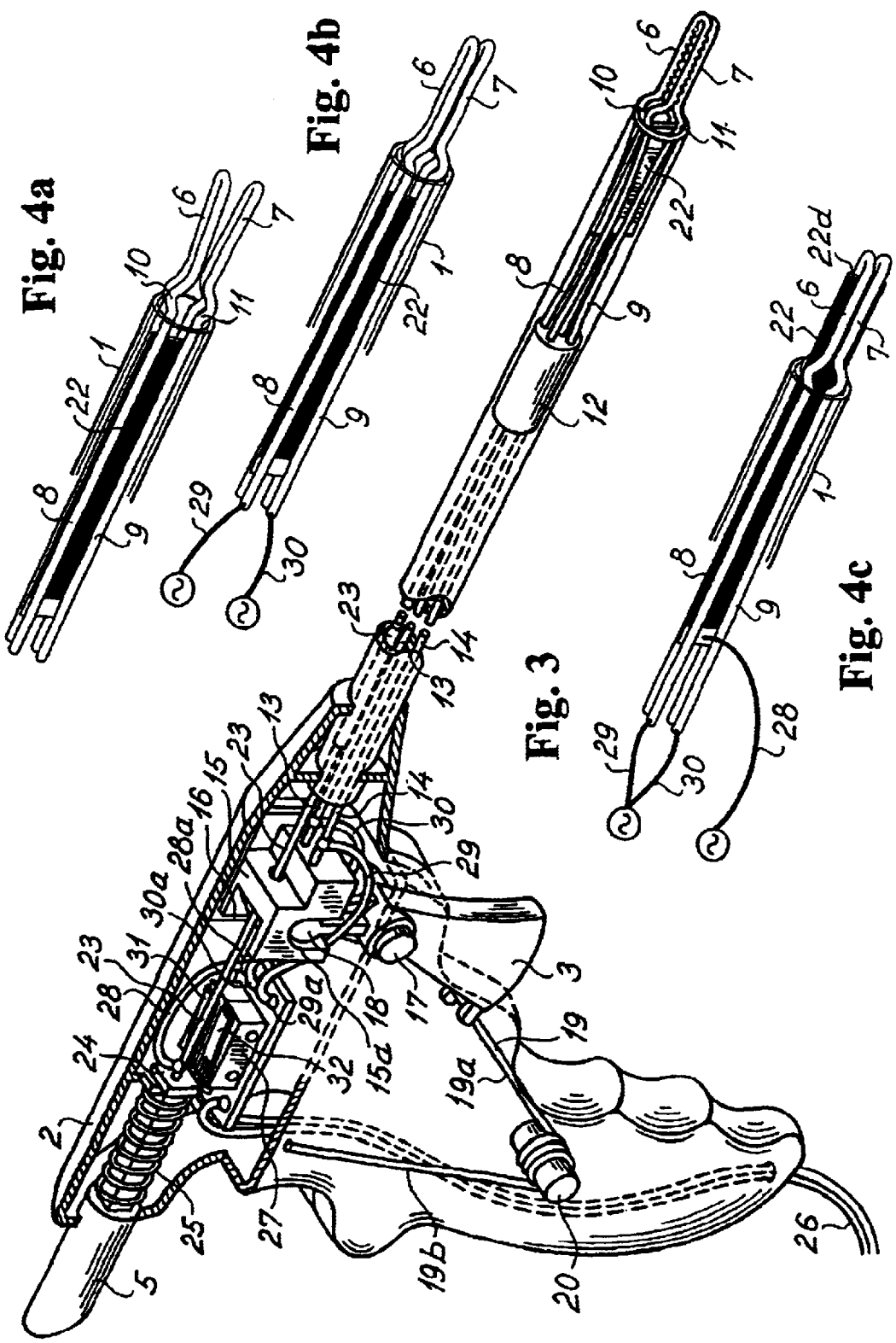

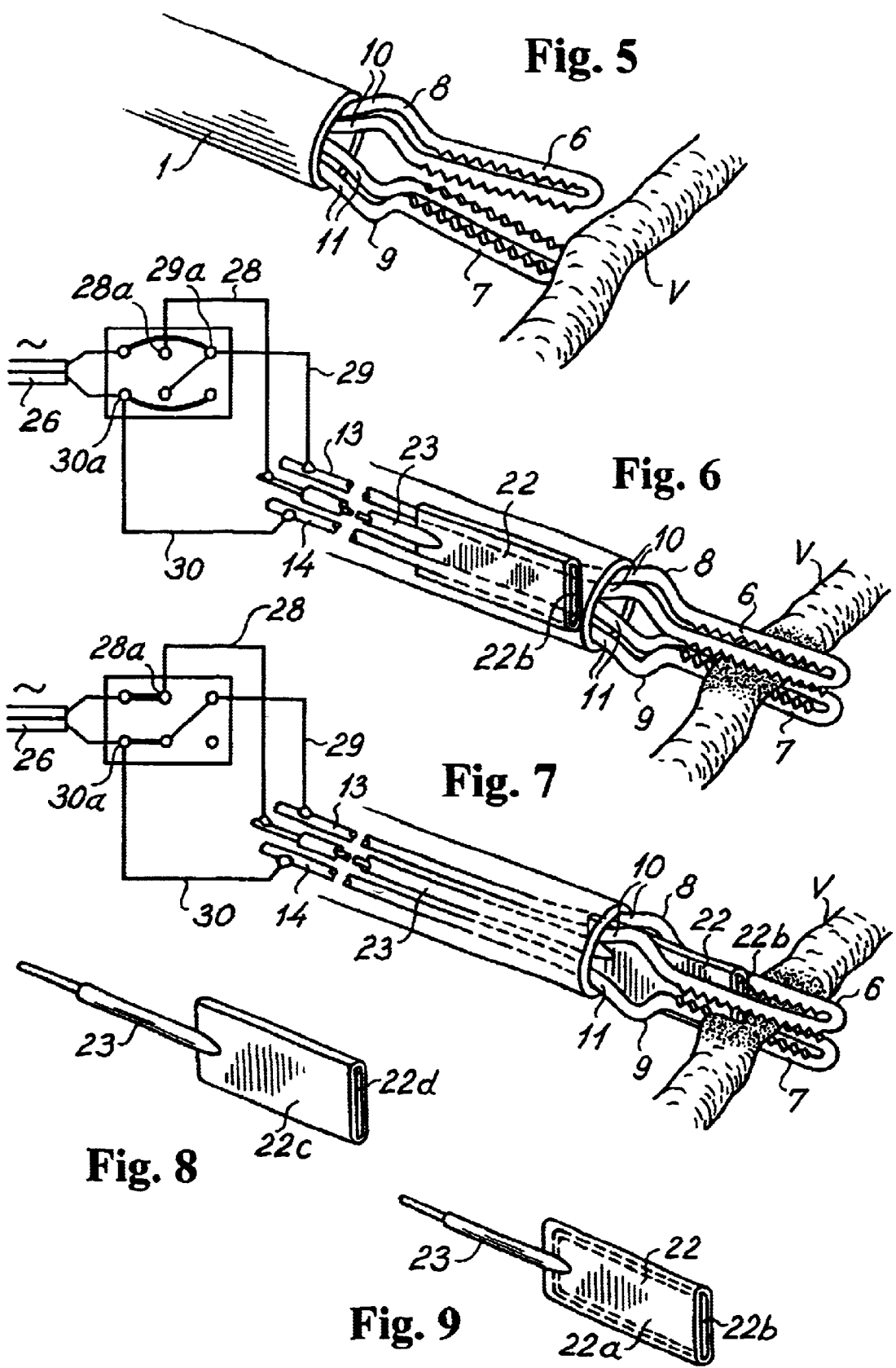

Figure 10:
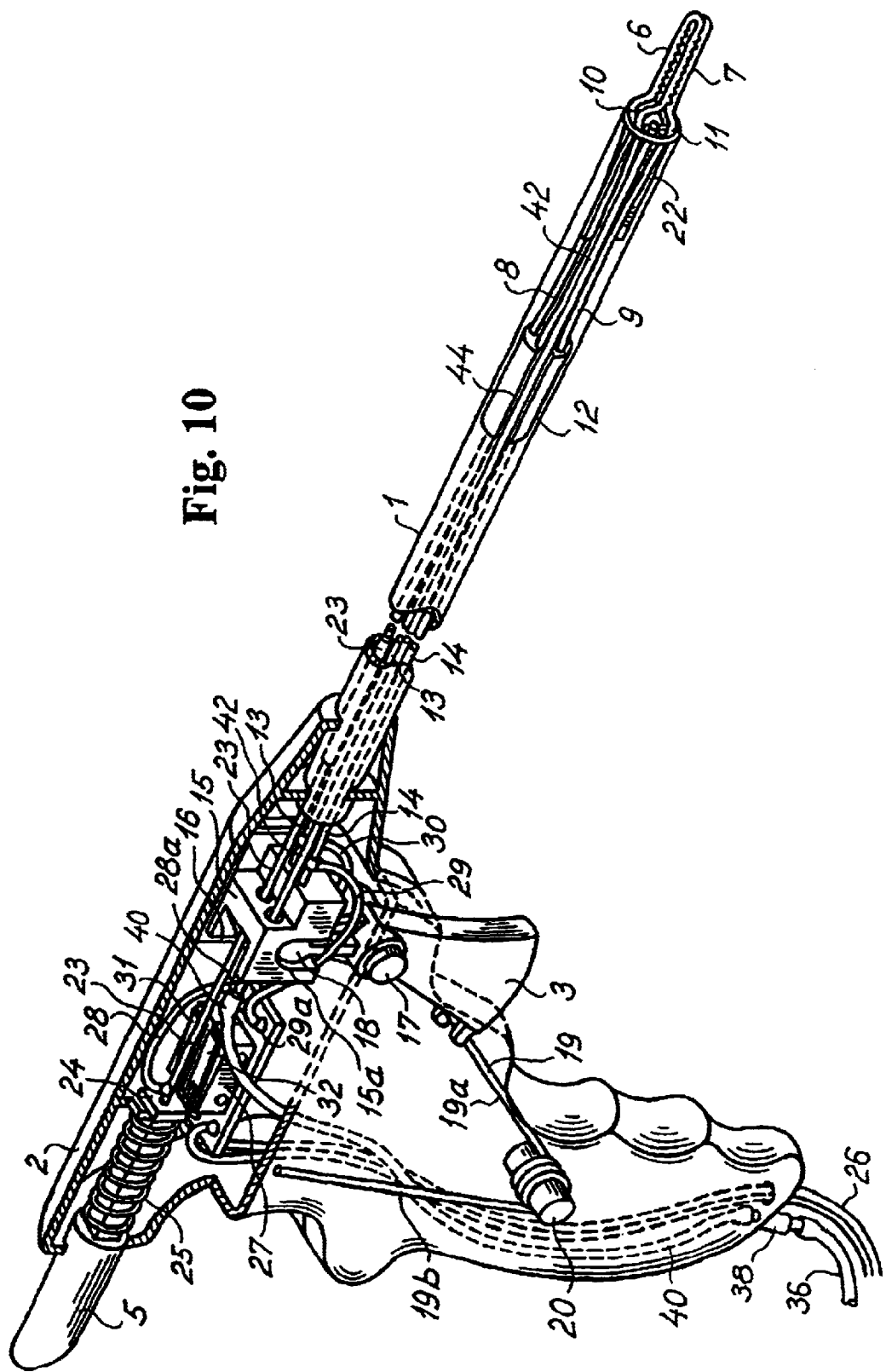

ELECTROSURGICAL DEVICE FOR COAGULATING AND FOR MAKING INCISIONS, A METHOD OF SEVERING BLOOD VESSELS AND A METHOD OF COAGULATING AND FOR MAKING INCISIONS IN OR SEVERING TISSUE

This is a Continuation-in-Part of application Ser. No. 09/310,773 filed May 10, 1999, now abandoned which is a Continuation-in-Part of PCT application Ser. No. PCT/DK98/00276 filed Jun. 22, 1998.

The present invention relates to an electrosurgical device for coagulating and for making incisions in or severing tissue such as for instance blood vessels, said device comprising at least one immobilizing means for immobilizing a tissue portion to be coagulated and incised and first electrical means for applying a first electric power to the tissue portion immobilized by the immobilizing means for coagulating at least part of said tissue portion.

An electrosurgical device of this type is disclosed in U.S. pat. No. 5,445,638 to Rydell et al. In this known device two moveable forceps jaws are provided for clamping the tissue portion therebetween, the forceps jaws being provided with electrical means to provide electric power for coagulating the tissue portion clamped therebetween. A cutting instrument with one or more cutting edges is provided for being moved between the forceps jaws for mechanically cutting the tissue portion after coagulation thereof has taken place.

When tissue such as for instance a blood vessel has been coagulated, the tissue often becomes relatively tough requiring a relatively large force to be exerted on the cutting instrument to perform the required incision. Furthermore each incision dulls the cutting edge thereby requiring even larger force for each incision. In many cases, the cutting edge has been dulled so much after one or two incisions that the device must be replaced if, as is often the case, several incision are to be performed during the same operation. As the device normally is intended to be discarded after use, this is expensive, and furthermore it is not desirable to have to re-move and introduce such devices during such surgery.

When tissue such as for instance a blood vessel or other tissue is coagulated through the supply of electric power to the blood vessel or other tissue, a risk exists of generating excessive carbonization or charting of the tissue through the supply of electric power to the tissue and further a disadvantage of generating smoke through the heating of the tissue in question through the evaporation of water and/or through possible carbonization or charring of the tissue through the supply of power to the tissue. It is to be understood that the generation of any excessive carbonization or charring of the tissue of a patient in itself constitutes a risk to the individuals' health and may cause serious injuries and possibly also give origin to cancer diseases It is also to be understood that the generation of smoke may on the one hand slow down the overall operation and prolongate the operation, which also may cause a risk to the patients' health, and on the other hand increasse the risk of the surgeon using the electrosurgical device incorrectly and thereby causing harm or injury to the patient.

Additionally, because of the toughness of the tissue and the manual application of the cutting force, the manipulation of the device is less smooth and easy than desirable, and the cutting operation may give rise to a snap-like reaction which is undesirable in this type of surgery.

A main object of the invention is thus to provide an electrosurgical device of the type in reference by means of which multiple incisions may be performed with the same device and without the disadvantages of the known device described above.

A further object of the invention is to provide an electrosurgical device of the type in reference by means of which the risk of generation of smoke through evaporation of water and/or carbonization or charring of the tissue through the supply of electric power to the tissue is to a great extent reduced or eliminated.

According to the invention, this object is achieved by providing the device with at least one electric power application means for applying a second electric power to at least part of said tissue portion for making incisions in said tissue portion, and by providing the device with at least one tubular element for supplying an electrically non-conductive, cooling liquid to the tissue portion, to which electric power is applied for making the incisions.

The invention, to be more precise, relates to an electrosurgical device for coagulation and for making incisions in or severing tissue such as for instance blood vessels, said device comprising:

- at least one immobilizing means for immobilizing a tissue portion to be coagulated and incised,
- first electrical means for applying a first electric power to the tissue portion immobilized by the immobilizing means for coagulating at least part of said tissue portion,
- at least one electric power application means for applying a second electric power to at least part of said tissue portion for making incisions in said tissue portion and
- at least one tubular element for supplying an electrically non-conductive, cooling liquid to said tissue portion.

Hereby, the second electric power applied gives rise to a thermal influence on the tissue portion whereby the incision is performed by the effects of the thermal influence which is not subject to alteration from incision to incision and therefore gives uniform handling characteristics as well as a smooth and easy operation because the toughness of the tissue has very reduced or no effect on the force to be exerted for performing the incision. By thermal Influence is meant herein the diverse effects of electric power applied to tissue and which are well known to those skilled in the art. Through the supply of the electrically non-conductive, cooling liquid to the tissue portion to which electric power is applied, the tissue is cooled and in particular any surface charring is to a great extent reduced or eliminated preventing the generation of smoke through charring and evaporation of water from the tissue.

Although, for some uses, it may be advantageous to combine a mechanical cutting effect with the thermal cutting effect for instance by providing the electric power application means according to the invention with a mechanical cutting edge, in the currently preferred device according to the invention, the electric power application means are configured such, for instance being blunt, that the incision or severing is substantially exclusively achieved by means of said second electric power.

Hereby it is achieved that the cutting characteristics of the device are not influenced at all by any dulling of a cutting edge. Furthermore, this feature is advantageous in that the risk of cutting through tissue that has not ben adequately coagulated for eliminating bleeding is greatly reduced or eliminated because the thermal effect of the second electric power applied by the electric power application means will tend to coagulate any tissue that has not been sufficiently coagulated by the application of the first electric power.

In the known device described above, the severing of a blood vessel, for instance, where the coagulation has not been performed correctly or in-sufficiently will give rise to bleeding when the blood vessel is severed by the cutting edge while the device according to the invention will tend to coagulate any insufficiently coagulated tissue or blood while performing the severing operation. This affords a device with a greatly increased safety margin whereby complications during surgery are reduced both in number and severity.

According to the invention and depending on the characteristics of the surgery to be performed, the first and/or the second electrical power may be constituted by an electric current signal, an electric voltage signal or a combination thereof, and the signal may be a DC or AC signal such as a LF, an HF or an RF signal for instance a VHF, a UHF or a microwave signal.

In the currently preferred embodiment of the device according to the invention, the first and second electric powers are obtained by means of substantially identical electric current or voltage signals. Hereby a common, relatively inexpensive signal generating means may be employed for generating the required signals. However, for some applications it may be advantageous that the respective electric current or voltage signals be different so as to obtain, for instance, a relatively higher incision power than coagulating power.

Although many different types of grasping means, pinning means and the like may be utilized as tissue immobilizing means, in the currently preferred embodiment of the device according to the invention, the immobilizing means comprise first and second moveable forceps jaws and moving means for opening and closing the first and second jaws relative to one another for holding and/or clamping the tissue portion therebetween.

When severing blood vessels it is important that the vessel be compressed to the correct degree to achieve the desired coagulation. Therefore, in the currently preferred embodiment of the device according to the invention, the moving means comprise adjustable spring loading means for applying a specific or an adjustable spring load for closing the first and second jaws relative to one another, and the spring load may be manually adjustable depending on the characteristics of the tissue portion to be held between said jaws. Hereby, the clamping effect may be adjusted according to the diameter, type and degree of calcification of the blood vessel to be severed. The surgeon may thus adjust the spring load and thereby the clamping effect prior to performing the severing of the blood vessel and thus avoid the inconvenience and complication of the known device described above where the surgeon must maintain the pressure manually during almost the whole severing operation.

In the currently preferred embodiment of the device according to the invention, the device furthermore comprises electrical switching means for applying the first and second electric powers independently of one another and preferably sequentially.

The currently preferred embodiment of the device according to the invention comprises:

an elongated tubular member having a proximal and a distal end and a lumen extending therethrough, first and second moveable forceps jaws extending from said distal end, opening and closing means for opening and dosing the first and second forceps jaws relative to one another, first electrical means for applying a first electric voltage across the first and second forceps jaws, an electric power application means extending from said distal end and arranged for being moved through a tissue portion held between the first and second forceps jaws, and second electrical means for applying a second electric voltage to the electric power application means relative to the first and/or the second forceps jaws.

Preferably, the first electric voltage is substantially equal to the second electric voltage.

The currently preferred embodiment of the device according to the invention further comprises a handle fixed to said proximal end of the tubular member, said handle advantageously comprising forceps activating means for manually activating the opening and closing means, spring load adjusting means for manually adjusting the spring load of the spring loading means, incision activating means for manually activating the movement of the electric power application means through the tissue portion, and switching means for activating the first and second electrical means for applying said first and second electric voltages.

So as to render the device according to the invention as practical as possible for the surgeon and avoid any risk of erroneous operation thereof, in the currently preferred embodiment of the device, the switching means are adapted to cooperate with the incision activating means such that the first electric voltage is applied in the deactivated condition of said incision activating means while the second electric voltage is applied in the activated condition of said incision activating means. Hereby the coagulating power is automatically succeeded by the incision power when the incision activating means are activated.

According to the currently preferred embodiment of the device according to the invention described above and including the tubular member and the handle, the said at least one tubular element is exposed at said distal end of said tubular member.

Further in the currently preferred embodiment of the device according to the invention, the said additional tubular element preferably includes a pump for controlling the supply of said electrically non-conductive, cooling liquid.

In the currently preferred embodiment of the device according to the invention the electric power application means comprise a plate member having a blunt leading edge, and the plate member except the leading edge portion is electrically insulated from the surroundings such that electric power only may be supplied to the tissue portion through said leading edge portion exclusively.

In an alternative embodiment of the device according to the invention, the electric power application means may advantageously comprise a wire member arranged for being moved through the tissue portion and for supplying electric power to the tissue portion.

The invention further relates to an electrosurgical device for coagulating and for making incisions in or severing tissue such as for instance blood vessels, said device comprising:

at least one immobilizing means for immobilizing a tissue portion to be coagulated and incised, first electrical means for applying electric power to the tissue portion immobilized by the immobilizing means for coagulating at least part of said tissue portion, at least one incision means for making incisions in at least part of said tissue portion, the immobilizing means comprising adjustable spring loading means for applying an adjustable spring load for immobilizing the tissue portion, and at least one tubular element for supplying an electrically non-conductive, cooling liquid to said tissue portion.

Preferably, the spring load is manually adjustable depending on the characteristics of the tissue portion to be immobilized by the immobilizing means.

In the currently preferred embodiment of the device according to the invention, the immobilizing means comprise first and second moveable forceps jaws and moving means for opening and closing the first and second jaws relative to one another for holding the tissue portion therebetween and the moving means comprise adjustable spring loading means for applying an adjustable spring load for closing the first and second jaws relative to one another.

The invention furthermore relates to a method of severing blood vessels, the method comprising the following steps:
  applying a first electric power to a portion of the blood vessel adjacent the intended severing location for coagulating the blood and tissue in said region,
  supplying an electrically nonconductive, cooling liquid to said portion of said blood vessel and/or to said region while applying said first and/or said second electric power, respectively, and
  applying a second electric power to said region at said severing location for severing the blood vessel.

Preferably, said portion of the blood vessel is compressed prior to and/or during the application of the first electric power, the degree of compression being such the blood and tissue coagulates to form a permanent coagulation clot in the blood vessel adjacent said severing location for allowing severing of the blood vessel without bleeding.

Advantageously, the first and/or the second electrical power is constituted by an electric current signal, an electric voltage signal or a combination thereof, and the signal is a DC or AC signal such as a LF, an HF or an RF signal for instance a VHF, a UHF or a microwave signal.

In the currently preferred embodiment of the method according to the invention, the first and second electric powers are obtained by means of substantially identical electric current or voltage signals.

Although any suitable values of the electric powers and any suitable signal frequency may be utilized for various purposes, in the currently preferred embodiment of the method according to the invention, the first and/or second electric powers are delivered by a 60 waft 500 kHz generator.

Finally, the Invention furthermore relates to a method of coagulating and for making incisions in or severing tissue such as for instance blood vessels, the method comprising the following steps:
  providing at least one immobilizing means for immobilizing a tissue portion to be coagulated and incised,
  providing first electrical means for applying a first electric power to the tissue portion immobilized by the immobilizing means for coagulating at least part of said tissue portion,
  providing at least one electric power application means for applying a second electric power to at least part of said tissue portion,
  immobilizing said tissue portion by applying said immobilizing means to the tissue portion,
  applying the electric power to the tissue portion for coagulating at least part of the tissue portion,
  applying the second electric power to at least part of said tissue portion for at least assisting in performing an incision in or severing the tissue portion, and supplying an electrically non-conductive, cooling liquid to said tissue portion while
  applying said first and/or said second electric power to said tissue portion.

Advantageously, the first and/or the second electrical power is constituted by an electric current signal, an electric voltage signal or a combination thereof, and the signal is a DC or AC signal such as a LF, an HF or an RF signal for instance a VHF, a UHF or a microwave signal.

In the currently preferred embodiment of the method according to the invention, the first and second electric powers are obtained by means of substantially identical electric current or voltage signals.

Although any suitable values of the electric powers and any suitable signal frequency may be utilized for various purposes, in the currently preferred embodiment of the method according to the Invention, particularly when being utilized for severing blood vessels, the first and/or second electric powers are delivered by a 60 Watt 500 kHz generator.

Although any suitable electrically nonconductive, cooling liquid may be used, experiments have revealed that the product Glycin ® has proven to fulfil the purpose of on the one hand allowing a cooling of the tissue to which electric power is applied and on the other hand preventing electric discharging from the tissue through conduction of electric current through the cooling liquid which would have occurred provided the cooling liquid was electrically conductive.

In the following a device according to the invention is described, solely by way of example, with reference to the accompanying drawings where:

FIG. 1 is a schematic perspective elevational view of a preferred embodiment of a device according to the invention, FIG. 2 is a schematic lateral partly cut-away view of the device in FIG. 1 shown in reduced scale, FIG. 3 is a schematic, partly sectional and perspective view of the device in FIG. 1

Figure 11:
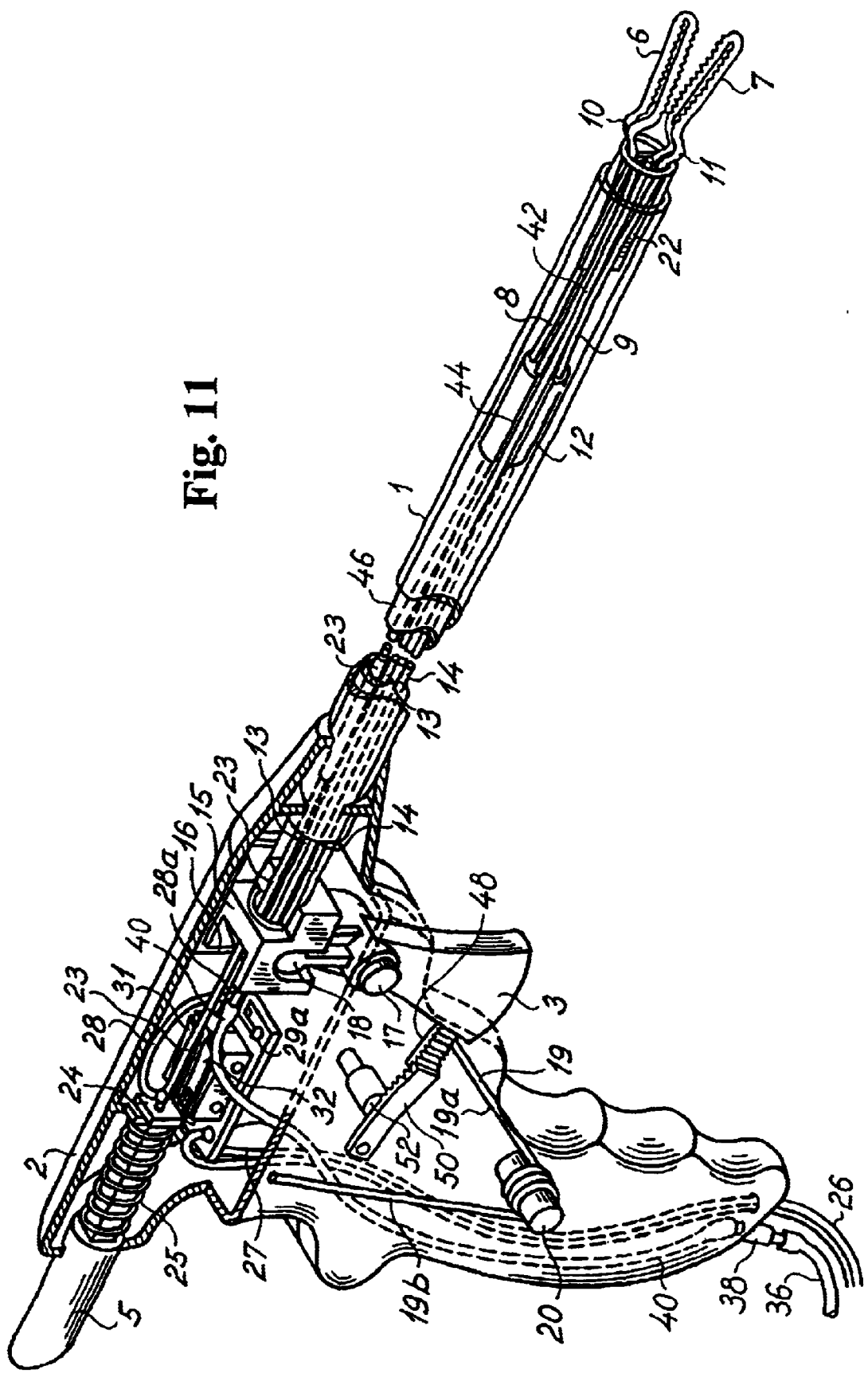

FIGS. 4a–c are partial diagrammatic illustrative views of three stages in the operation of device in FIG. 1, FIGS. 5–7 are partial diagrammatic illustrative views illustrating the operation of the device in FIG. 1 when utilized for severing a blood vessel, FIG. 8 is a diagrammatic view of one embodiment of an electric power application means according to the invention shown in increased scale, FIG. 9 is a diagrammatic view of a second embodiment of an electric power application means according to the invention shown in increased scale, FIG. 10 is a schematic, partly sectional and perspective view similar to the view of FIG. 3 illustrating the device in FIGS. 1 and 3 including a cooling liquid applying tube, and FIG. 11 is a schematic, partly sectional and perspective view similar to the views of FIGS. 3 and 10 illustrating a modified device as compared to the device shown in FIG. 10

Referring now to FIGS. 1–3, the currently preferred embodiment of an electrosurgical device according to the invention comprises an elongate rigid tube 1 made from a glass fiber reinforced tubing material, with a vinyl ester resin as the matrix the material being of the type Polygon II CW produced by the Polygon Company but may be made from any suit-able material having sufficient strength and being substantially electrically non-conductive. At one end, the proximal end, the tube 1 is fixedly attached to a handle 2 provided with a trigger lever 3, a spring load adjustment knob 4 and a severing activating push button 5.

Two forceps jaws 6 and 7 protrude from the distal end of the tube 1, the jaws 6 and 7 each being formed by bending a length of steel wire 8 and 9, respectively, so as to form the jaws 6 and 7 and camming portions 10 and 11, respectively, the two end portions of each wire 8 and 9 being embedded in an electrically non-conductive cylinder 12 longitudinally slideably arranged in the lumen of the tube 1. The lengths of wire 8 and 9 are furthermore bent such that a spring force is achieved tending to force the jaws 6 and 7 away from one another, the jaws being forced to abut each other in the de-activated condition of the device shown in FIG. 3 by the cooperation of the distal edge of the tube 1 and the camming portions 10 and 11.

The cylinder 12 is fixedly attached to the distal ends of two rigid, electrically conductive rods 13 and 14 that are electrically connected to the wires 8 and 9, respectively, and the rods 13 and 14 are attached at the proximal ends thereof to an electrically non-conductive block 15 longitudinally slideably arranged in guide members 16 arranged on the lateral inner surfaces of the handle 2. The trigger lever 3 is pivotably arranged about a pivot 17 and is provided with a protuberance 18 engaging a recess 15a in the block 15 such that pivoting of the trigger lever 3 around the pivot 17 causes the block 15 to slide to and fro longitudinally in the guide members 16 in the handle 2. Movement of the block 15 in,the distal direction causes the cylinder 12 and the wires 8 and 9 to move in the distal direction whereby the forceps jaws 6 and 7 move away from each other because of said spring force in[]the wires 8 and 9 and the cooperation between the camming portions 10 and 11 with the distal edge of the tube 1.

When the trigger lever 3 is fully depressed the forceps jaws 6 and 7 are in the open position shown in FIG. 5. When the trigger lever 3 is in the de-activated position, the block 15 is at its furthermost proximal position and the forceps jaws abut each other because of the inherent spring force in the wires 8 and 9 and the camming cooperation between the camming portions 10 and 11 and the distal edge of the tube 1. However, the force achieved by this cooperation is relatively weak and not sufficient to clamp and compress a blood vessel as shown in FIG. 6. Therefore an additional spring force is applied to move the forceps jaws 6 and 7 towards one another as explained below.

A coil spring 19 with two arms 19a and 19b is arranged on a pin 20, the end of the arm 19a being pivotably attached to the trigger lever 3 and the end of the arm 19b being pivotably attached to a protuberance 4a of the knob 4, the knob 4 and protuberance 4a being slideably arranged in an arcuate slot 21 in the handle 2. The spring force applied to the trigger lever 3 by the coil spring 19 is thus adjustable by sliding the protuberance in the slot 21. The spring force applied to the trigger lever 3 biases the block 15 in the proximal direction thereby exerting a relatively large force for moving the forceps jaws 6 and 7 towards one another and for clamping and compressing a blood vessel therebetween. The shape and orientation of the slot 21 relative to the spring 19 and the pin 20 determine the number of possible settings of the spring force exerted by the spring 19. In this embodiment, a maximum spring force and a minimum spring force are obtainable by placing the knob 4 at the left and right end of the slot 21, respectively.

Referring now to FIGS. 3 and 4a–c, an elongate plate shaped electric power application electrode or member 22 is slideably arranged in the lumen of the tube 1 such that it may slide longitudinally from a retracted position entirely within the distal portion of the tube 1 as shown in FIGS. 3 and 4a–b and an extended position shown in FIG. 4c protruding from the tube 1 and located between the two legs of each forceps jaw 6 and 7. The proximal end of the electrode 22 is fixedly attached to the distal end of a rigid electrically conductive rod 23 extending slideably through a central bore in the cylinder 12 and slideably through a bore in the block 15, the proximal end of the rod 23 being fixedly attached to a plate member 24 attached to the push button 5 arranged longitudinally slidable in an aperture in the handle 2 under the biassing influence of a coil spring 25. The rod 23 is along the length thereof extending in the lumen of the tube 1 surrounded by an electrically insulating material.

By depressing the push button 5 in the distal direction against the biassing force of the coil spring 25, the rod 23 is displaced longitudinally in the distal direction thereby displacing the electrode 22 in the distal direction from the retracted to the extended position thereof while the action of the coil spring 25 will reverse this displacement when pressure is not applied to the push button 5 thereby retracting the electrode 22 into the distal end of the tube 1.

Referring now to FIGS. 8 and 9, two alternative embodiments of the electric power application electrode or member 22 are illustrated. In FIG. 9 the electrode comprises an electrically insulated proximal body 22a and an electrically uninsulated distal wire 22b electrically connected to the rod 23. In FIG. 8 the electrode comprises a plate member electrically connected to the rod 23 and having an electrically insulated body 22c having an electrically uninsulated distal blunt edge 22d. Neither the wire 22b nor the blunt edge 22d are able to perform any mechanical cutting function on any tissue when the electrode 22 is displaced from the retracted proximal position to the extended distal position thereof. The insulating material utilized for the electrical insulation of the body region of the electrode is black polyvinylidene fluoride of the type KBM-100 produced by Plastronics US, Inc. of Alpharetta, Ga. 30201.

Referring now to FIG. 3, a power cable 26 leading from a 60 Watt 500 kHz generator (not shown) is connected to an electrical switch 27 that will be described more in detail in the following. An electrical lead 28 electrically interconnects a terminal 28a of the switch 27 and the rod 23 and thereby the electrode 22. Electrical leads 29 and 30 electrically interconnect terminals 29a and 30a, respectively, of the switch 27 with the rods 13 and 14, respectively, and thereby with the wires 8 and 9, respectively.

Referring now to FIGS. 6 and 7 an electrical diagram of the switch 27 is shown illustrating that in the situation shown in FIG. 6 wherein a blood vessel V is clamped between the forceps jaws 6 and 7 voltage is applied across the forceps jaws as the terminal 29 and 30 are electrically connected to the power cable 26 and thereby to the generator whereby a coagulation of the tissue and blood between the jaws takes place. In the situation shown in FIG. 7 a voltage is applied across the uninsulated wire 22b or the uninsulated tip region 22d of the electrode 22 in an extended position of said electrode 22 and both the forceps jaws 6 and 7 thereby giving rise to a thermal influence of the tissue adjacent the wire 22b or the tip region 22d and particularly the edge 22e.

The switching function of the switch 27 between the coagulating position of FIG. 6 and the severing position of FIG. 7 is achieved by means of two spring tongues 31 and 32 arranged on the top surface of the switch 27, the spring tongues being depressed by the plate 24 when the push button 5 is displaced in the distal direction.

Referring now to FIG. 10, a modified embodiment of the device shown in FIG. 3 is illustrated, which embodiment includes all elements of the embodiment described above with reference to FIG. 3, further includes a tubular element 42 which extends parallel with the rods 13 and 14 within the outer protective elongated rigid tube 1. The tubular element is, as is evident from FIG. 10, exposed at the outer opened end or distal end of the elongated rigid tube 1. The tubular element 42 extends through the block 15 and is at its' proximate end opposite to the above-described distal end, connected to a tube 40 connected to a fitting 38 at the lower end of the handle 2 for allowing connection to an external container through which an electrically non-conductive, cooling liquid is supplied to the tissue portion which is to be coagulated or separated through the supply of electrical power to the tissue portion in question.

The cooling liquid has to be electrically non-conductive in order to prevent that the liquid short circuits the location of applying electrical power which short circuiting might else give origin to extreme injuries at unintentional tissue locations within the body of the patient. The electrically non-conductive, cooling liquid may preferably be constituted by the liquid known as Glycin®.

In FIG. 11, a further embodiment, slightly differing from the embodiment shown in FIG. 10 is illustrated, which embodiment basically differs from the embodiment described in that the forceps 6 and 7 are operated in the inverse mode of operation, as the forceps 6 and 7 in the above-described embodiment illustrated in FIGS. 1–10 are kept in the closed position through the application of pressure to the trigger lever 3 from the spring 19 and consequently kept in the closed position provided the trigger lever 3 is not operated and opened through the actuation of the trigger lever 3, whereas the forceps 6 and 7 are in the embodiment shown in FIG. 11 kept in their open position, provided the trigger lever 3 is not operated and pressed together by the actuation of the trigger lever 3.

In the embodiment shown in FIG. 11, the spring 19 serves to force the trigger lever 3 to its' neutral position in which the forceps 6 and 7 are seperated apart. For establishing the inverse operation of the forceps 6 and 7 in the embodiment shown in FIG. 11 as compared to the above-described embodiments, a further tubular element 46 is provided, which tubular element is a movable inner tube in relation to the outer rigid tube 1.

In FIG. 10, the rods 13 and 14 of the forceps 6 and 7 are connected to the block 10 and movable along with the block 15 shown in FIG. 10, whereas in FIG. 11, the forceps 6 and 7 and consequently the rods 13 and 14 connected thereto are stationary in relation to the handle 2, whereas the block 15 causes the inner tube 46 to move in relation to the outer rigid tube 1 and further in relation to the forceps 6 and 7 and causing through the application of pressure to the camming portions 10 and 11 a motion of the forceps 6 and 7 towards one another provided the trigger lever 3 be actuated and the block 15 and along with the block 15, the inner tube 46 be extracted from the outer rigid tube 1.

For maintaining the forceps 6 and 7 in a specific close position, a ratchet catch is provided in the handle which ratchet catch comprises two cooperating ratchet elements 48 and 50 which are connected to the trigger lever 3 and the housing of the handle 2, respectively, and serve to maintain the trigger lever 3 in a specific position after actuation and thereby also maintaining the forceps 6 and 7 in a corresponding specific position applying a manually set pressure load to the blood vessel or other tissue kept between the forceps 6 and 7.

For disengaging the ratchet elements 48 and 50 from their locking the trigger lever 13 in a preset position, a push button 52 is provided, which protrudes from the outer remote side of the handle 2 and serves to apply a pressure to the ratchet element 50 and cause the ratchet element 50 to be disengaged from the ratchet element 48 through actuation of the push button 52.

In use, the surgeon operating the device first decides which spring load to set by means of the knob 4 depending on the character of the tissue portion, for instance the blood vessel to be severed. Thereafter the surgeon depresses the trigger lever 3 so as to separate the forceps jaws 6, 7 relative to one another, FIG. 5. The forceps jaws are then placed around the vessel and the trigger lever 3 is released so that the forceps jaws are retracted slightly and are moved towards one another by the action of the spring 19, FIG. 6 and the cooperation between the camming portions 10 and 111 and the distal end of the tube 1. The voltage across the forceps jaws coagulates the tissue and any blood in the vessel therebetween. Thereafter the surgeon gradually depresses the push button 5 thereby extending the electrode 22 and simultaneously and automatically switching the voltage from coagulation mode across the forceps jaws 6 and 7 to the severing mode across the electrode 22 and both jaws 6, 7, FIG. 7.

In use, the surgeon may, by means of the embodiments illustrated in FIGS. 10 and 11 apply electrically nonconductive, cooling liquid to the tissue portion to be coagulated or separated through the application of electric energy or power to the tissue portion by actuating a pump supplying electrically nonconductive, cooling liquid for ejection from the outer exposed distal end of the tube 42 through the supply of the liquid through the hose 36. The pump may be continuously running or be operated in an intermittent mode for interrupting the supply of cooling liquid or alternatively the hose 36 may be provided with a hose pump which is periodically operated or stopped or alternatively be provided with a blocking element preventing the supply of liquid through the hose 36.

As no mechanical cutting effect is involved, the toughness of the tissue to be severed has no effect on the force to be exerted on the push button 5, and the severing action is smooth and gradual with no snap effect as with known mechanical cutting instruments in the known devices.

The person skilled in the art will readily understand that many of the features described above in relation to the embodiment shown in the drawings may be varied and modified without departing from the scope of the invention as defined in the appended patent claims.

Thus, the electrode may have any suitable shape such as pointed, bifurcated, spherical, cylindrical and so on as long as sufficient thermal influence can be caused by the electrical power applied to the electrode.

As mentioned above, the electrode may, for certain applications, have a mechanically cutting edge so as to be able to utilize mechanical cutting in addition to the thermal influence cutting However, the security of the device will thereby be impaired as the risk of cutting through not sufficiently coagulated tissue or blood vessels will be higher as discussed above.

The diameter of the tube 1 may be any suitable value such as 5 mm or 10 mm and the materials chosen for the various components may be modified as long as the requirements of biological non-toxicity and sterility are met.

The spring loading of the immobilizing means such as the described forceps jaws or any other suitable immobilizing means may be achieved by other means than the described coli spring, for instance a cylinder-piston mechanism with adjustable pressure.

The tube 2 may be replaced by any other suitable means for locating the immobilizing means and electrical power application means adjacent the tissue to be coagulated and incised, for instance two or three parallel or concentric tubes, one or two for the immobilizing means and one for the electric power application means.

EXAMPLE

DIMENSIONS

Total length of device parallel to axis of tube 1: 465 mm.
Handle size: 75×145×20 mm
Tube 1 or cannula: 300 mm
Cannula diameter 10 mm Forceps size: 1.5 mm wire, U-form 4.5×25 mm (closed)

Plate electrode: 22×6.2×0.28 mm

Cable: 3 meter with 2×4 male connector

COMPONENTS

Handle+push button+trigger lever: Material: ABS

Cannula: Material: Vinyl ester resin with glass fibre reinforcement

Forceps; Material: Stainless steel spring wire (AISI 302)

Plate electrode: Material: Stainless steel covered by KYNAR KBM 100

Connector: Material: Nickel plated brass with plastic housing

Cable: Material: CU with PVC insulation

Sterialization of entire device by electron irradiation.

For contemplated smaller diameters of the tube 1, for instance 5 mm, the rigidity achievable with glass fibre reinforced vinyl ester resin matrix may not be sufficient and therefore it is contemplated to make the tube 1 of stainless steel. In such case the regions of the forceps jaw wires 8 and 9 extending from the cylinder 12 to the distal end of the camming portions 10 and 11, i.e. the regions of the wires being able to come into contact with the distal edge of the tube 1, are contemplated being electrically insulated by means of KYNAR KBM 100 to avoid electrical connection between the forceps jaws and the tube 1.

Test of Cutting Function

Objective

To examine the possible advantage of applying an active electrode to perform the cutting function compared to a sharp blade with mechanical cutting function.

The objective is based on the statements from surgeons using a similar device where they claimed that the mechanical cutting blade became blunt.

Test

Three tests were conducted on a piece of meat:

1. Transection with a mechanically cutting blade ; After coagulating the meat with the forceps, the sharp cutting blade was advanced through the meat. This procedure was repeated several times (on fresh meat zones) while monitoring/sensing the blade's cutting ability.

Conclusion: After having repeated the procedure 6 times there was a clear difference in the smoothness of the cutting function. The blade seemed to push the meat out of the forceps and more pressure had to be applied to perform the transection.

2. Transection with a non-active blunt electrode (without applying electric power): After coagulating the meat with the forceps, the blunt electrode was advanced to perform transection.

Conclusion: The blunt electrode could hot cut its way through the meat, but instead pushed it out of the forceps. The electrode could only make a very rough and uncontrolled preliminary cut when pressed forward with a very strong force.

3. Transection with an active blunt electrode: After coagulating the meat with the forceps, the active electrode was advanced to perform transection. The active electrode performed the cutting very smoothly, and the resistance to the meat was clearly minimized, hence the self cutting effect of the electric power or electrosurgical energy.

Conclusion: This procedure was performed continuously for 25 times and the electrode performed the cutting smoothly and without damage to the meat. There seemed no reason why it should not be able to continue cutting the meat. Only the electrode had to be cleaned once due to meat adhering on the edge.

Final Conclusion

From the above tests, it was concluded that the active electrode gave a significantly better long term performance and an incision which was fully acceptable compared to a mechanically cutting blade. In fact, the active electrode seemed to perform a superficial coagulation of the incision, thus securing a complete coagulation of blood vessels.

What is claimed is:

1. An electrosurgical device for coagulating and for making incisions in or severing tissue such as for instance blood vessels, said device comprising:

at least one immobilizing means for immobilizing a tissue portion to be coagulated and incised, first electrical means for applying electric power to the tissue portion immobilized by the immobilizing means for coagulating at least part of said tissue portion, at least one blunt incision means for making incisions in at least part of said tissue portion, and the immobilizing means comprising adjustable spring loading means for applying an adjustable spring load for immobilizing the tissue portion.

2. A device according to claim 1 wherein the spring load is manually adjustable depending on the characteristics of the tissue portion to be immobilized by the immobilizing means.

3. A device according to claim 1 wherein the immobilizing means comprise first and second moveable forceps jaws and moving means for opening and closing the first and second jaws relative to one another for holding the tissue portion therebetween.

4. A device according to claim 3 wherein the moving means comprise adjustable spring loading means for applying an adjustable spring load for closing the first and second jaws relative to one another.

5. An electrosurgical device for coagulating and for making incisions in or severing tissue such as for instance blood vessels, said device comprising:

at least one immobilizing means for immobilizing a tissue portion to be coagulated and incised, first electrical means for applying a first electric power to the tissue portion immobilized by the immobilizing means for coagulating at least part of said tissue portion, at least one second electrical me for applying a second electric power to at least part of said tissue portion for making incisions in said tissue portion at least one tubular element for supplying an electrically non-conductive, cooling liquid to said tissue portion, and the second electrical means is configured such, by being blunt, that the incision or severing is substantially exclusively achieved by means of said second electric power.

6. A device according to claim 5 wherein the first and/or the second electrical power is constituted by an electric current signal, an electric voltage signal or a combination thereof.

7. A device according to claim 6 wherein the signal is a DC or AC signal such as a LF, an BF or an RF signal for instance a VHF, a UHF or a microwave signal.

8. A device according to claim 5 wherein the first and second electric powers are obtained by means of substantially identical electric current or voltage signals.

9. A device according to claim 5 wherein the immobilizing means comprise first and second moveable forceps jaws and moving means for opening and closing the first and second jaws relative to one another for holding and/or clamping the tissue portion therebetween.

10. A device according to claim 9 wherein the moving means comprise adjustable spring loading means for applying a specific or an adjustable spring load for closing the first and second jaws relative to one another.

11. A device according to claim 10 wherein the spring load is manually adjustable depending on the characteristics of the tissue portion to be held between said jaws.

12. A device according to claim 5 and further comprising electrical switching means for applying the first and second electric powers independently of one another and preferably sequentially.

13. An electrosurgical device for coagulating and for making incisions in or severing tissue such as for instance blood vessels, said device comprising
- at least one immobilizing means for immobilizing a tissue portion to be coagulated and incised,
- first electrical means for applying a first electric power to the tissue portion immobilized by the immobilizing means for coagulating at least part of said tissue portion,
- at least one second electrical means for applying a second electric power to at least part of said tissue portion for making incisions in said tissue portion,
- at least one tubular element for supplying an electrically non-conductive, cooling liquid to said tissue portion, and
- the second electrical means is configured such, by being blunt, that the incision or severing is substantially exclusively achieved by means of said second electric power.

14. A device according to claim 13 wherein the first and/or the second electrical power is constituted by an electric current signal, an electric voltage signal or a combination thereof.

15. A device according to claim 14 wherein the signal is a DC or AC signal such as a LF, an HF or an RF signal for instance a VHF, a UHF or a microwave signal.

16. A device according to claim 13 wherein the first and second electric powers are obtained by means of substantially identical electric current or voltage signals.

17. A device according to claim 13 wherein the immobilizing means comprise first and second moveable forceps jaws and moving means for opening and closing the first and second jaws relative to one another for holding and/or clamping the tissue portion therebetween.

18. A device according to claim 17 wherein the moving means comprise adjustable spring loading means for applying a specific or an adjustable sprig load for closing the first and second jaws relative to one another.

19. A device according to claim 18 wherein the spring load is manually adjustable depending on the characteristics of the tissue portion to be held between said jaws.

20. A device according to claim 13 and further comprising electrical switching means for applying the first and second electric powers independently of one another and preferably sequentially.

21. An electrosurgical device for coagulating and for making incisions in or severing tissue such as for instance blood vessels, said device comprising:
- an elongated tubular member having a proximal and a distal end and a lumen extending therethrough,
- first and second moveable forceps jaws extending from said distal end,
- opening and closing means for opening and closing the first and second forceps jaws relative to one another,
- first electrical means for applying a first electric voltage across the first and second forceps jaws,
- a blunt electric power application means extending from said distal end and arranged for being improved through a tissue portion held between the first and second forceps jaws, and
- second electrical means for applying a second electric voltage to the electric power application means relative to the first and/or the second forceps jaws.

22. A device according to claim 21 wherein the first electric voltage is substantially equal to the second electric voltage.

23. A device according to claim 21 and further comprising a handle fixed to said proximal end of the tubular member.

24. A device according to claim 23 wherein the opening and closing means comprise adjustable spring loading means for applying a specific or an adjustable spring load for closing the first and second jaws relative to one another.

25. A device according to claim 24 wherein the handle comprises spring load adjusting means for manually adjusting the spring load of the spring loading means.

26. A device according to claim 23 wherein the handle comprises forceps activating means for manually activating the opening and closing means.

27. A device according to claim 23 wherein the handle comprises incision activating means for manually activating the movement of the electric power application means through the tissue portion.

28. A device according to claim 23 wherein the handle comprises switching means for activating the first and second electrical means for applying said first and second electric voltages.

29. A device according to claim 28 wherein the switching means are adapted to cooperate with the incision activating means such that the first electric voltage is applied in the deactivated condition of said incision activating means while the second electric voltage is applied in the activated condition of said incision activating means.

30. A device according to claim 21 wherein the blunt electric power application means comprise a plate member having a blunt leading edge.

31. A device according to claim 30 wherein the plate member except the leading edge portion is electrically insulated from the surroundings such that electric power only may be supplied to the tissue portion through said leading edge portion.

32. A device according to claim 21 wherein the blunt electric power application means comprise a wire member arranged for being moved through the tissue portion and for supplying electric power to the tissue portion.

33. A method of severing blood vessels, the method comprising the following steps:
- applying a first electric power to a portion of the blood vessel adjacent the intended severing location for coagulating the blood and tissue in said region, and
- applying a second electric power to said region at said severing location by means of a blunt electric power application means for severing the blood vessel.

34. A method according to claim 33 wherein said portion of the blood vessel is compressed prior to and/or during the application of the first electric power, the degree of compression being such that the flow of blood through the blood vessel is such that the blood and tissue for coagulates to form a permanent coagulation clot in the blood vessel adjacent said severing location for allowing severing of the blood vessel without bleeding.

35. A method according to claim 33 wherein the first and/or the second electrical power is constituted by an electric current signal, an electric voltage signal or a it combination thereof.

36. A method according to claim 33 wherein the signal is a DC or AC signal such as a LF, an HF or an RF signal for instance a VHF, a UHF or a microwave signal.

37. A method according to claim 33 wherein the first and second electric powers are obtained by means of substantially identical electric current or voltage signals.

38. A method according to claim 36 wherein the first and/or second electric powers are delivered by a 60 Watt 500 kHz generator.

39. A method of coagulating and for making incisions in or severing tissue such as for instance blood vessels, the method comprising the following steps:

providing at least one immobilizing means for immobilizing a tissue portion to be coagulated and incised, providing first electrical means for applying a first electric power to the tissue portion immobilized by the immobilizing means for coagulating at least part of said tissue portion, providing at least one electric power application means for applying a second electric power to at least part of said tissue portion, immobilizing said tissue portion by applying said immobilizing means to the tissue portion, applying the first electric power to the tissue portion for coagulating at least part of the tissue portion, and applying the second electric power to at least part of said tissue portion by means of a blunt incision means for at least assisting in performing an incision in or severing the tissue portion.

40. A method according to claim 39 wherein the first and/or the second electrical power is constituted by an electric current signal, an electric voltage signal or a combination thereof.

41. A method according to claim 40, wherein the signal is a DC or AC signal such as a LF, an HF or an RF signal for instance a VHF, a UHF or a microwave signal.

42. A method according to claim 40 wherein the signal is a DC or AC signal such as a LF, an BY or an RF signal for instance a VHF, a UHF or a microwave signal.

43. A method according to claim 39 wherein the first and second electric powers are obtained by means of substantially identical electric current or voltage signals.

44. A method according to claim 39 wherein the first and/or second electric powers are delivered by a 60 Watt 500 kHz generator.

45. An electrosurgical device for coagulating and for making incisions in or severing tissue such as for instance blood vessels, said device comprising:

an elongated tubular member having a proximal and a distal end and a lumen extending therethrough, first and second moveable forceps jaws extending from said distal end, opening and closing means for opening and closing the first and second forceps jaws relative to one another, first electrical means for applying a first electric voltage across the first and second forceps jaws, a blunt electric power application means extending from said distal end and arranged for being moved through a tissue portion held between the first and second forceps jaws, at least one tubular element for supplying an electrically non-conductive, cooling liquid to said tissue portion, and second electrical means for applying a second electric voltage to the electric power application means relative to the first and/or the second forceps jaws.

46. A device according to claim 45 wherein the first electric voltage is substantially equal to the second electric voltage.

47. A device according to claim 45 and further comprising a handle fixed to said proximal end of the tubular member.

48. A device according to claim 47 wherein the opening and closing means comprise adjustable spring loading means for applying a specific or an adjustable spring load for closing the first and second jaws relative to one another.

49. A device according to claim 48 wherein the handle comprises spring load adjusting means for manually adjusting the spring load of the spring loading means.

50. A device according to claim 47 wherein the handle comprises forceps activating means for manually activating the opening and closing means.

51. A device according to claim 47 wherein the handle comprises incision activating means for manually activating the movement of the electric power application means through the tissue portion.

52. A device according to claim 47 wherein the handle comprises switching means for activating the first and second electrical means for applying said first and second electric voltages.

53. A device according to claim 47, wherein said at least one tubular element extends from said handle through said elongated tubular member and communicates through a fiber tubular element with an external source for the supply of said electrically non-conductive, cooling liquid.

54. A device according to claim 53, wherein said at least one tubular element is exposed at said distal end of said tubular member.

55. A device according to claim 53, wherein said further tubular element comprises a pump for controlling the supply of said electrically non-conductive, cooling liquid.

56. A device according to claim 47, wherein the switching means are adapted to cooperate with the incision activating means such that the first electric voltage is applied in the deactivated condition of said incision activating means while the second electric voltage is applied in the activated condition of said incision activating means.

57. A device according to claim 45, wherein the electric power application means comprise a plate member having a blunt leading edge.

58. A device according to claim 47, wherein the plate member except the leading edge portion is electrically insulated from the surroundings such that electric power only may be supplied to the tissue portion through said leading edge portion.

59. A device according to claim 45, wherein the electric power application means comprise a wire member arranged for being moved through the tissue portion and for supplying electric power to the tissue portion.

60. A device according to claim 45, said electrically non-conductive, cooling liquid being Glycin®.

61. An electrosurgical device for coagulating and for making incisions in or severing tissue such as for instance blood vessels, said device comprising at least one immobilizing means for immobilizing a tissue portion to be coagulated and incised, first electrical means for applying electric power to the tissue portion immobilized by the immobilizing means for coagulating at least part of said tissue portion, at least one blunt incision means for making incisions in at least part of said tissue portion, and at least one tubular element for supplying an electrically non-conductive, cooling liquid to said tissue portion, the immobilizing means comprising adjustable spring loading means for applying an adjustable spring load for immobilizing the tissue portion.

62. A device according to claim 61, wherein the spring load is manually adjustable depending on the characteristics of the tissue portion to be immobilized by the immobilizing means.

63. A device according to claim 61, wherein the immobilizing means comprise first and second moveable forceps jaws and moving means for opening and closing the first and second jaws relative to one another for holding the tissue portion therebetween.

64. A device according to claim 63, wherein the moving means comprise adjustable spring loading means for applying an adjustable spring load for closing the first and second jaws relative to one another.

65. A method of severing blood vessels, the method comprising the following steps:

applying a first electric power to a portion of the blood vessel adjacent the intended severing location for coagulating the blood and tissue in said region, applying a second electric power to said region at said severing location by means of a blunt electric power application means for severing the blood vessel, and supplying an electrically non-conductive, cooling liquid to said portion of said blood vessel and/or to said region while applying said first and/or said second electric power, respectively.

66. A method according to claim 65, wherein said portion of the blood vessel is compressed prior to and/or during the application of the first electric power, the degree of compression being such that the flow of blood through the blood vessel is such that the blood and tissue for coagulates to form a permanent coagulation clot in the blood vessel adjacent said severing location for allowing severing of the blood vessel without bleeding.

67. A method according to claim 65, wherein the first and/or the second electrical power is constituted by an electric current signal, an electric voltage signal or a combination thereof.

68. A method according to claim 65, wherein the signal is a DC or AC signal such as a LF, an HF or an RF signal for instance a VHF, a UHF or a microwave signal.

69. A method according to claim 65, wherein the first and second electric powers are obtained by means of substantially identical electric current or voltage signals.

70. A method according to claim 68, wherein the first and/or second electric powers are delivered by a 60 Watt 500 kHz generator.

71. A method of coagulating and for making incisions in or severing tissue such as for instance blood vessels, the method comprising the following steps:

providing at least one immobilizing means for immobilizing a tissue portion to be coagulated and incised, providing first electrical means for applying a first electric power to the tissue portion immobilized by the immobilizing means for coagulating at least part of said tissue portion, providing at least one electric power application means for applying a second electric power to at least part of said tissue portion, immobilizing said tissue portion by applying said immobilizing means to the tissue portion, applying the first electric power to the tissue portion for coagulating at least part of the tissue portion, and applying the second electric power to at least part of said tissue portion by means of a blunt incision means for at least assisting in performing an incision in or severing the tissue portion, supplying an electrically non-conductive, cooling liquid to said tissue portion while applying said first and/or said second electric power to said tissue portion.

72. A method according to claim 71, wherein the first and/or the second electrical power is constituted by an electric current signal, an electric voltage signal or a combination thereof.

73. A method according to claim 71, said electrically non-conductive, cooling liquid being Glycin®.

74. A method according to claim 71, wherein the first and second electric powers are obtained by means of substantially identical cleric current or voltage signals.

* * * * *

UNITED STATES PATENT AND TRADEMARK OFFICE
CERTIFICATE OF CORRECTION

PATENT NO. : 6,679,882 B1
DATED : January 20, 2004
INVENTOR(S) : Kornerup

It is certified that error appears in the above-identified patent and that said Letters Patent is hereby corrected as shown below:

Column 1,
Line 8, "This is a continuation-in-Part" should read -- This application is a Continuation-in-Part --
Line 11, "Jun. 22, 1998." should read -- Jun. 22, 1998 and a Continuation of PCT application Serial No. PCT/DK99/00565, filed 15 October 1999. --
Line 53, "diseases It is" should read -- diseases. It is --
Line 57, "other hand increase the risk" should read -- other hand increase the risk --

Column 2,
Line 39, "By thermal Influence is meant" should read -- By thermal influence is meant --

Column 5,
Line 22, "being such the blood" should read -- being such that the blood --
Line 39, "60 waft 500 kHz" should read -- 60 watt 500 kHz --

Column 6,
Line 18, "has proven to fulfil" should read -- has proven to fulfill --

Column 7,
Line 20, "in, the distal direction" should read -- in the distal direction --
Line 23, "in[]the wires 8" should read -- in the wires 8 --

Column 8,
Lines 66-67, "and is at its' proximate" should read -- and is at its proximate --

Column 10,
Line 42, "cutting However, the" should read -- cutting. However, the --

Column 11,
Line 60, "could hot cut its" should read -- could not cut its --

Column 12,
Line 54, "electrical me for" should read -- electrical means for --
Line 56, "said tissue portion" should read -- said tissue portion, --

Column 13,
Line 2, "BF or an RF" should read -- HF or an RF --
Line 25, "said device comprising" should read -- said device comprising: --
Line 59, "adjustable sprig load" should read -- adjustable spring load --

UNITED STATES PATENT AND TRADEMARK OFFICE
CERTIFICATE OF CORRECTION

PATENT NO. : 6,679,882 B1
DATED : January 20, 2004
INVENTOR(S) : Kornerup

It is certified that error appears in the above-identified patent and that said Letters Patent is hereby corrected as shown below:

Column 14,
Line 13, "being improved through" should read -- being moved through --

Column 15,
Lines 11-12, "or a it combination" should read -- or a combination --
Line 50, "an BY or an RF" should read -- an HF or an RF --
Line 53, "according to claim 39" should read -- according to claim 40 --

Column 16,
Line 36, "through a fiber" should read -- through a further --
Line 67, "said device comprising" should read -- said device comprising: --
Line 47, "identical cleric current" should read -- identical electric current --

Signed and Sealed this

Twenty-fourth Day of August, 2004

JON W. DUDAS
*Director of the United States Patent and Trademark Office*